(12) United States Patent
Kalb

(10) Patent No.: US 8,835,649 B2
(45) Date of Patent: Sep. 16, 2014

(54) METHOD OF SYNTHESIZING ORGANIC MOLECULES USING IONIC LIQUIDS COMPRISING A CARBANION

(75) Inventor: Roland Kalb, Leoben (AT)

(73) Assignee: VTU Holding GmbH, Grambach (AT)

( * ) Notice: Subject to any disclaimer, the term of this patent is extended or adjusted under 35 U.S.C. 154(b) by 189 days.

(21) Appl. No.: 13/380,705

(22) PCT Filed: Jun. 22, 2010

(86) PCT No.: PCT/EP2010/058860
§ 371 (c)(1),
(2), (4) Date: Feb. 13, 2012

(87) PCT Pub. No.: WO2010/149675
PCT Pub. Date: Dec. 29, 2010

(65) Prior Publication Data
US 2012/0136161 A1 May 31, 2012

(30) Foreign Application Priority Data
Jun. 25, 2009 (EP) .................................... 09163829

(51) Int. Cl.
| | | |
|---|---|---|
| *C07D 233/58* | (2006.01) | |
| *C07C 381/12* | (2006.01) | |
| *C07D 207/06* | (2006.01) | |
| *C07D 233/08* | (2006.01) | |
| *C07D 339/08* | (2006.01) | |
| *C07C 69/72* | (2006.01) | |
| *C07D 233/06* | (2006.01) | |
| *C07D 213/20* | (2006.01) | |
| *C07C 211/63* | (2006.01) | |
| *C07C 49/12* | (2006.01) | |

(52) U.S. Cl.
CPC ............ *C07D 207/06* (2013.01); *C07C 381/12* (2013.01); *C07D 233/08* (2013.01); *C07D 339/08* (2013.01); *C07C 69/72* (2013.01); *C07D 233/06* (2013.01); *C07D 213/20* (2013.01); *C07C 211/63* (2013.01); *C07C 49/12* (2013.01)
USPC ...................................................... 548/335.1

(58) Field of Classification Search
None
See application file for complete search history.

(56) References Cited

FOREIGN PATENT DOCUMENTS

WO 2006007703 A1 1/2006

OTHER PUBLICATIONS

Jain et al. Catal. Lett. 2007, 115, 52-55.*
Zhou et al. Chinese J. Chem. 2008, 26, 1469-1480.*
Carey et al. "Carbanions and Other Nucleophilic Carbon Species." Advanced Organic Chemistry 5th ed., Part A: Structure and Mechanism. New York: Kluwer Academic/Plenum Publishers, 2007. Chapter 6, pp. 579-619.*
Brand et al. "Nonlinear, Resonance-Stabilized Pseudohalides: From Alkali Methanides to Ionic Liquids of Methanides" Eur. J. Inorg. Chem. 2006, 21, 4924-4308.*
Li et al. "Fluorine-Containing Ionic Liquids from N-Alkylpyrrolidine and N-Methylpiperidine and Fluorinated Acetylacetones: Low Melting Points and Low Viscosities" Eur. J. Inorg. Chem. 2008, 21, 3353-3358.*
Brindaban, C. Ranu et al., "Ionic Liquids as Catalysts and Reaction Medium—A Simple, Efficient and Green Procedure for Knoevenagel Condensation of Aliphatic and Aromatic Carbonyl Compounds", European Journal of Organic Chemistry, Jun. 19, 2006, pp. 3767-3770, XP002595221.
Brindaban, C. Ranu et al., "Ionic Liquid as a Catalyst and Reaction Medium. The Dramatic Influence of a Task-Specific Ionic Liquid, [bmIm]OH, in Michael addition of Active Methylene Compounds to Conjugated Ketones, Carboxylic Esters, and Nitriles", Organic Letters, Jul. 7, 2005, LNKD-PUBMED: 15987202, vol. 7, No. 14, pp. 3049-3052, XP002595222.
Sun et al., "Ionic Liquids as Efficient Phase-Transfer Catalysts for the Solid Base-Promoted Monoalkylation of Diethyl Malonate", Chinese Chemical Letters, Elsevier LTD., GB LNKD-DOI:10.1016/J.CCLET.2007.01.028, vol. 18, No. 3, Feb. 23, 2007, pp. 279-282, XP005943344.
Zicmanis, Andris et al., "Alkylation of Ambient Indole Anion in Ionic Liquids," Central European Journal of Chemistry, DOI: 10.2478/s11532-006-0063-8, vol. 5., No. 1, Mar. 1, 2006, pp. 156-168, XP019469995.

* cited by examiner

*Primary Examiner* — Michael Barker
*Assistant Examiner* — Amanda L Aguirre
(74) *Attorney, Agent, or Firm* — Robert A. Blaha; Smith Risley Tempel Santos LLC

(57) ABSTRACT

A method of synthesizing organic molecules is provided, wherein the method comprises providing an electrophilic educt, providing an ionic liquid comprising a carbanion, and synthesizing the organic molecules by mixing the electrophilic educt and the ionic liquid.

8 Claims, No Drawings

METHOD OF SYNTHESIZING ORGANIC MOLECULES USING IONIC LIQUIDS COMPRISING A CARBANION

TECHNICAL FIELD

The invention relates to a method of synthesizing organic molecules, in particular for synthesizing organic molecules by using carbanions.

Moreover the invention relates to a method of producing an ionic liquid, in particular for producing an ionic liquid comprising a carbanion.

BACKGROUND

Carbanions, i.e. anions having negative charge at the respective carbon atom, are known and play an important role in the organic synthesis to facilitate C—C bonding, i.e. to construct or form carbon structures. Such carbanions may act as a carbon based nucleophile which may react with suitable electrophiles, e.g. by substitution reactions, addition reaction and radical reaction. Possible reactions may be in particular alkylation by using alkylhalogenides or alkylsulfates, Wittig reaction or Horner-Emmons reaction, olefination, aldol reaction, Michael-addition or -condensation, Dieckmann condensation, Claisen condensation, Knoevenagel condensation, ylide rearrangement, Japp-Klingemann reaction, Tafel rearrangement, malonic ester synthesis, or the like.

However, the known methods for synthesizing organic molecules may not be suitable for all carbanions or may at least exhibit low reaction rates.

SUMMARY

It may be an objective of the invention to provide a method of synthesizing organic molecules which may exhibit improved reactivity. Furthermore, it may be an object of the invention to provide a method of producing an ionic liquid.

This object may be solved by a method of synthesizing organic molecules and a method of producing an ionic liquid, according to the independent claims. Further exemplary embodiments are described in the dependent claims.

According to an exemplary aspect a method of synthesizing organic molecules is provided, wherein the method comprises providing an electrophilic educt, providing an ionic liquid comprising a carbanion, and synthesizing the organic molecules by mixing the electrophilic educt and the ionic liquid.

In particular, no solvent except the ionic liquid may be necessary. That is, the ionic liquid may form one educt, namely the anion, and at the same time may form a solvent as well, so that no other solvent may be necessary. In particular, the electrophilic educt may form an electrophile with respect to the carbanion. The mixing may enable a reaction of the carbanion and the electrophilic educt, for example.

According to an exemplary aspect a method of producing an ionic liquid comprising a carbanion including a first ion is provided, wherein the method comprises providing a primary ionic liquid comprising the first ion as a cation and a base as an anion, and mixing the primary ionic liquid with a C—H acid. In particular, volatile components may be removed at a temperature less than 100° C., particularly at temperatures less than 70° C. and preferably at temperatures less than 50° C. If necessary, reduced pressure may be used.

Ionic liquids are liquid organic salts or mixtures of salt consisting of organic cations and organic or inorganic anions and having a melting point of less than 100° C. Additionally inorganic salts and/or additives may be solved in these ionic liquids. These ionic liquids exhibit some very interesting characteristics, e.g. having a very low, virtually non-measurable, vapor pressure, a high liquidus range, good electrical conductivity, and interesting solvation characteristics. These characteristics may predestine ionic liquids for several applications, e.g. as solvents (for example, in organic or inorganic synthesis, transition metal catalysis, biocatalysis, multiphase reactions, photochemistry, polymer synthesis, and nanotechnology), extracting agent (for example, liquid-liquid or liquid gaseous extraction, sulphur removal during crude oil processing, removal of heavy metals during water processing and liquid membrane extraction), electrolytes (for example, in batteries, fuel cells, capacitors, solar cells, sensors, in electrochemistry, electroplating, electrochemical metal processing, electrochemical synthesis, electroorganic synthesis, and nanotechnology), lubricants, thermofluids, gels, reagents for organic synthesis, in the so-called "green chemistry" (e.g. as replacement for volatile organic compounds), static inhibitors, specific applications in chemical analysis (e.g. gas chromatography, mass spectroscopy, capillary zone electrophoresis), and liquid crystals, etc. More details may be found in "Rogers, Robin D.; Seddon, Kenneth R. (Eds.); Ionic Liquids—Industrial Applications to Green Chemistry, ACS Symposium Series 818, 2002; ISBN 0841237891" and in "Wasserscheid, Peter; Welton, Tom (Eds.); Ionic Liquids in Synthesis, Verlag Wiley-VCH 2003; ISBN 3527305157". The characteristics of ionic liquids may be adapted to any desired application by varying the respective anions and cations. Due to this wide variety of possible characteristics ionic liquids are often called "designer solvents".

It should be noted that according to this application the term "ionic liquid" may also include liquid organic salts or mixtures of salts comprising organic cations and organic or inorganic anions and having a melting point of less than 200° C. That is, the term "ionic liquid" may also include molten salts having a melting point of more than 100° C. but less than 200° C., since these ionic liquids do not differ in their other characteristics from ionic liquids having a melting point of less than 100° C. which is typically the melting point threshold according to the prior art.

A preferred method or process to form carbanions is the deprotonation of C—H acids by using bases, which are stronger bases as the formed carbanions. In particular, in case that the acidity of the hydrogen bounded to the carbon is increased or boosted by electrophilic and/or mesomeric stabilizing functional groups, since these groups may delocalize and stabilize a resulting negative charge. The forming of such carbanions may be relatively easy. Some typical functional groups may be keto groups, carbonic acid ester groups, cyano groups, etc. In particular, the deprotonation may be readily achievable in case that two of such functional groups are present, e.g. in case of acetyl acetonates (upper portion), or malonic acid dialkylesters (lower portion, as diethylester):

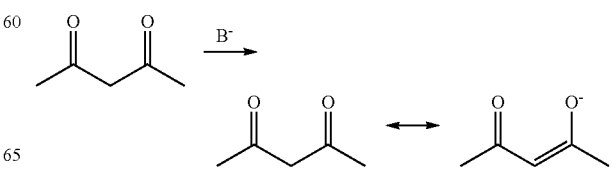

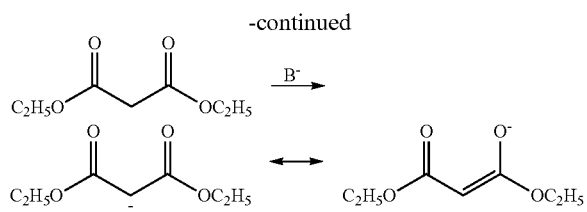

Bases which may be used for deprotonating, may be hydroxides, alcoholates, Hünig's base, DBU (1,8-diazabicyclo[5.4.0]undec-7-ene), amides in liquid ammonia, alkyllithium compounds, etc. The above depicted anions are mesomeric stabilized, so that the negative charge is present partly at the C atom and partly at the O atom. However, it should be noted that according to this application the term "carbanion" may include all structures or chemical compounds which are formed or produced by deprotonating a C—H acid, independent of the fact whether the main part of the charge is present at the C atom or whether it is delocalized or blurred due to inductive or mesomeric effects. Only the possibility of the anion to act as a carbon based nucleophile and to effect C—C bonding reactions may be important.

By using carbanions which are part of an ionic liquid it may be possible to increase the reaction rate. Furthermore, it may be possible to increase the speed and yield of organic molecules. In some cases a reaction may even be enabled only due to the use of a carbanion which forms part of an ionic liquid. In particular, improvements may be caused since no other solvents may be necessary so that reactions of the electrophilic educt and the carbanion may directly proceed or be performed in the ionic liquid. In other words the ionic liquid may be, by its carbanion, reacting agent (educt) and solvent at the same time. Thus, the concentration of the reacting anion may be maximal while at the same time an increased reactivity may be possible since the carbanion is not solved in a conventional solvent, but in "itself". Furthermore, it may be simple to separate the product (organic molecule) from the educts since the ionic liquid has a very low vapor pressure. Since the ionic liquid is a molten salt and not a solution of ions in a solvent based on solvents, the ionic liquid may only comprise ions. Thus, in general these ions are not solvated so that no solvate envelope may be present so that they may not be sterically impeded or impeded by electric effects, which may lead to an improved reaction rate.

Next, further aspects of exemplary embodiments of the method of synthesizing organic molecules are described. However, the aspects may also be valid for the method of producing an ionic liquid.

According to an exemplary embodiment of the method the ionic liquid satisfy the generic formula $[Q^+]_a[A^{a-}]$, wherein a is 1, 2 or 3.

In particular, $[Q^+]$ may be one out the group consisting of quaternary ammonium cation $[R^1R^{1'}R^2R^3N]^+$, phosphonium $[R^1R^{1'}R^2R^3P]^+$, sulfonium $[R^1R^{1'}R^2S]^+$ and a hetero aromatic cation. However, tetramethylammonium, tetraethylammonium and tetrabutylammonium may be excluded only in combination with acetylacetonate and dialkylmalonate carbanions.

Specific examples may be:

$R^1$, $R^{1'}$, $R^2$, $R^3$ may be alkyl, alkenyl, alkinyl, cycloalkyl, cycloalkenyl, aryl or heteroaryl which may be independently substituted, or two of the moieties $R^1$, $R^{1'}$, $R^2$, $R^3$ may form a ring together with a hetero-atom to which they are bound. The ring may be saturated, unsaturated, substituted or unsubstituted. The chain may be interrupted by one or more hetero-atoms out of the group consisting of O, S, NH or N—$C_1C_4$-alkyl, and an heteroaromate cation may be 5 or 6 membered heteroaromate comprising at least one N atom and if necessary one O atom and/or one S atom. The heteroaromate may be substituted or unsubstituted and/or annelated. Preferably, the heteroaromate is selected from the group consisting of:

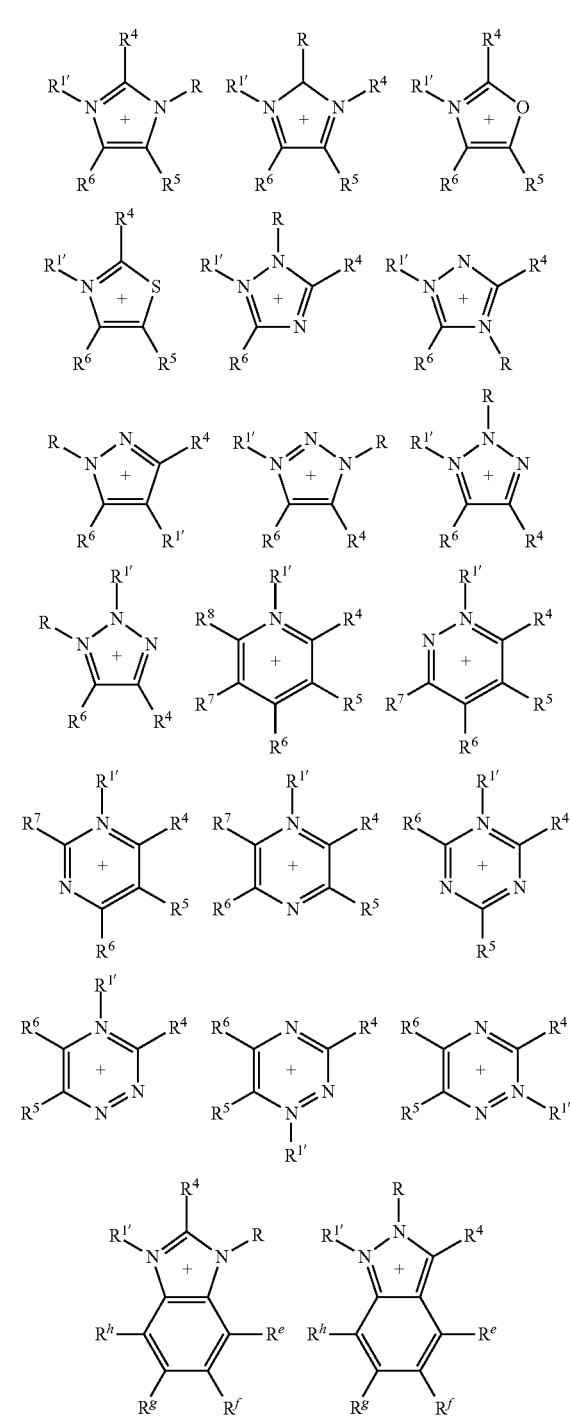

-continued

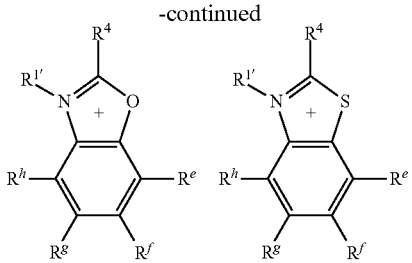

wherein the moiety R may be one of the following:

R hydrogen, $C_1$-$C_{30}$-alkyl, $C_3$-$C_{12}$-cycloalkyl, $C_2$-$C_{30}$-alkenyl, $C_3$-$C_{12}$-cycloalkenyl, $C_2$-$C_{30}$-alkinyl, aryl oder heteroaryl, wherein the latter 7 moieties may have one or more halogenic moiety and/or 1 to 3 moieties selected from the group consisting of $C_1$-$C_6$-alkyl, aryl, heteroaryl, $C_3$-$C_2$-cycloalkyl, halogen, $OR^c$, $SR^c$, $NR^cR^d$, $COR^c$, $COOR^c$, CO—$NR^cR^d$, wherein $R^c$ and Rd may be hydrogen, $C_1$-$C_6$-alkyl, $C_1$-$C_6$-halogenalkyl, cyclopentyl, cyclohexyl, phenyl, tolyl oder benzyl;

$R^1$, $R^{1'}$, $R^2$, $R^3$ may be hydrogen, alkyl, alkenyl, alkinyl, cycloalkyl, cycloalkenyl, aryl or heteroaryl which may be independently substituted; or two of the moieties $R^1$, $R^{1'}$, $R^2$, $R^3$ may form a ring together with a hetero-atom to which they are bound. The ring may be saturated, unsaturated, substituted or unsubstituted. The chain may be interrupted by one or more hetero-atoms out of the group consisting of O, S, NH or N—$C_1C_4$-alkyl;

$R^4$, $R^5$, $R^6$, $R^7$, $R^8$ may be, independently of each other, hydrogen, halogen, nitro, cyano, $OR^c$, $SR^c$, $NR^cR^d$, $COR^c$, $COOR^c$, CO—$NR^cR^d$, alkyl, $C_3$-$C_{12}$-cycloalkyl, $C_2$-$C_{30}$-alkenyl, $C_3$-$C_{12}$-cycloalkenyl, aryl or heteroaryl, wherein the latter 6 moieties may comprise one or more halogenic moiety and/or 1 to 3 moieties selected out of the group consisting of $C_1$-$C_6$-alkyl, aryl, heteroaryl, $C_3$-$C_7$-cycloalkyl, halogen, $OR^c$, $SR^c$, $NR^cR^d$, $COR^c$, $COOR^c$, CO—$NR^cR^d$, wherein $R^c$ and $R^dR^d$ may be, independently of each other, hydrogen, $C_1$-$C_6$-alkyl, $C_1$-$C_6$-halogenalkyl, cyclopentyl, cyclohexyl, phenyl, tolyl oder benzyl; or two neighboring moieties of the moieties R, $R^4$, $R^5$, $R^6$, $R^7$, $R^8$, may form, together with an atom they are bound, a ring which may be unsaturated or aromatic, unsaturated or saturated, wherein the chain formed by the respective moieties may be interrupted by one or more hetero-atoms out of the group consisting of O, S, NH or N—$C_1C_4$-alkyl;

$R^e$, $R^f$, $R^g$, $R^h$, may be, independently of each other, hydrogen, $C_1$-$C_6$-alkyl, aryl-, heteroaryl-, $C_3$-$C_7$-cycloalkyl, halogen, $OR^c$, $SR^c$, $NR^cR^d$, $COOR^c$, CO—$NR^cR^d$, oder $COR^c$, wherein $R^c$, $R^d$, may be, independently of each other, hydrogen, $C_1$-$C_6$-alkyl, $C_1$-$C_6$-halogenalkyl, cyclopentyl, cyclohexyl, phenyl, tolyl oder benzyl; preferably for hydrogen, halogen, $C_1$-$C_6$-alkyl, in particular, hydrogen or $C_1$-$C_6$-alkyl.

According to an exemplary embodiment of the method of synthesizing organic molecules the ionic liquid satisfy the generic formula $[Q^+][A^-]$, wherein the anion can be written by one of

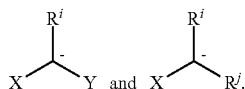

In particular, the anion may be describable by the resonant or mesomeric states and/or may have a negative charge of 1, 2 or 3:

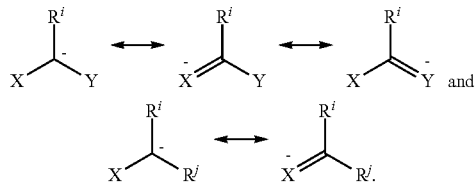

wherein X and Y may indicate, independently from each other, groups which may attract electrons due to the inductive effect or the mesomeric effect and/or which may delocalize and/or stabilize (localize) electrons. Examples for such groups may be:

—CN, —$NO_2$, —$NO_3$, —CO—$R^k$, —$COOR^k$, —C=N—$R^k$, —CO—$NR^kR^m$, —$NR^kR^m$, —OH, —$OR^k$, —SH, —$SR^k$, —SO—$R^k$, —$SO_2$—$R^k$, —$SO_2$—$OR^k$, —PO—$OR^kOR^m$ (phosphonate), —I, —Cl, —Br, —F, —$CCl_3$, —$CCl_2R^k$, —$CCIR^kR^m$, —$CF_3$, —$CF_2R^k$, —$CFR^kR^m$, —$SO_2CF_3$, —$COOCF_3$, —$C_6H_5$, —$CR^k=CR^mR^n$, —$C\equiv CR^m$, —$CR^k=CR^m$—CN, —$CR^k=CR^m$—$NO_2$, —$CR^k=CR^m$—CO—$R^k$, —$CR^k=CR^m$—$COOR^k$, —$CR^k=CR^m$—C=N—$R^n$, —$CR^k=CR^m$—CO—$NR^nR^o$, —$CR^k=CR^m$—$NR^nR^o$, —$CR^k=CR^m$—$OR^n$, —$CR^k=CR^m$—$SR^n$, —$CR^k=CR^m$—$SO_2$—$R^n$, —$CR^k=CR^m$—$SO_2$—$R^n$, —$CR^k=CR^m$—$SO_2$—Rn, —$CR^k=CR^m$—$SO_2OR^n$, —$CR^k=CR^m$—$CF_3$, —$CR^k=CR^m$—$SO_2CF_3$, wherein $R^k$, $R^m$, $R^n$, $R^o$ may, independently from each other, denote hydrogen, $C_1$- to $C_{30}$-alkyl and their aryl-, heteroaryl-, cycloalkyl-, halogen-, hydroxy-, amino-, carboxy-, formyl-, —O—, —CO—, —CO—O— or —CO—N< substituted components, like methyl, ethyl, 1-propyl, 2-propyl, 1-butyl, 2-butyl, 2-methyl-1-propyl(isobutyl), 2-methyl-2-propyl (tert.-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl(benzyl), diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl, methoxy, ethoxy, formyl, acetyl oder $C_nF_{2(n-a)+(1-b)}H_{2a+b}$ wherein n≤30, 0≤a≤n and b=0 or 1 (e.g. $CF_3$, $C_2F_5$, $CH_2CH_2$—$C_{(n-2)}F_{2(n-2)+1}$, $C_6F_{13}$, $C_8F_{17}$, $C_{10}F_{21}$, $C_{12}F_{25}$);

$C_3$- to $C_{12}$-cycloalkyl and their aryl-, heteroaryl-, cycloalkyl-, halogen-, hydroxy-, amino-, carboxy-, formyl-, —O—, —CO— or —OC—O— substituted components, e.g. cyclopentyl, 2-methyl-1-cyclopentyl, 3-methyl-1-cyclopentyl, cyclohexyl, 2-methyl-1-cyclohexyl, 3-methyl-1-cyclohexyl, 4-methyl-1-cyclohexyl or $C_nF_{2(n-a)-(1-b)}H_{2a-b}$ wherein n≤0, 0≤a≤n and b=0 or 1;

$C_2$- to $C_{30}$-alkenyl and their aryl-, heteroaryl-, cycloalkyl-, halogen-, hydroxy-, amino-, carboxy-, formyl-, —O—, —CO— or —CO—O-substituted components, e.g. 2-propenyl, 3-butenyl, cis-2-butenyl, trans-2-butenyl or $C_nF_{2(n-a)-(1-b)}H_{2a-b}$ wherein n≤30, 0≤a≤n and b=0 or 1;

$C_3$- to $C_{12}$-cycloalkenyl and their aryl-, heteroaryl-, cycloalkyl-, halogen-, hydroxy-, amino-, carboxy-, formyl-, —O—, —CO— or —CO—O-substituted components, e.g. 3-cyclopentenyl, 2-cyclohexenyl, 3-cyclohexenyl, 2,5-cyclohexadienyl or $C_nF_{2(n-a)-3(1-b)}H_{2a-3b}$ wherein n≤0, 0≤a≤n and b=0 or 1; and aryl oder heteroaryl having 2 to 30 carbon atoms and their alkyl-, aryl-, heteroaryl-, cycloalkyl-, halogen-, hydroxy-, amino-, carboxy-, formyl-, —O—, —CO— or —CO—O-substituted components, e.g. phenyl, 2-methyl-phenyl (2-tolyl), 3-methyl-phenyl (3-tolyl), 4-methyl-phenyl, 2-ethyl-phenyl, 3-ethyl-phenyl, 4-ethyl-phenyl, 2,3-dimethyl-phenyl, 2,4-dimethyl-phenyl, 2,5-dimethyl-phenyl, 2,6-dimethyl-phenyl, 3,4-dimethyl-phenyl, 3,5-dimethyl-phenyl, 4-phenyl-phenyl, 1-naphthyl, 2-naphthyl, 1-pyrrolyl, 2-pyrrolyl, 3-pyrrolyl, 2-pyridinyl, 3-pyridinyl, 4-pyridinyl or $C_6F_{(5-a)}H_a$ wherein 0≤a≤5, wherein pairs of the $R^k$, $R^m$, $R^n$, $R^o$ may be bonded directly to each other or via C1-C4, which may be substituted if necessary, so that a saturated, unsaturated, or conjugated unsaturated ring may be formed.

According to an exemplary embodiment of the method of synthesizing organic molecules the ionic liquid satisfy the generic formula $[Q^+]_a[A^{a-}]$, wherein $[A^{a-}]$ is a carbanion with the formal negative charge a–, which is formed by deprotonating one chemical compound out of the group consisting of: dialkyl ketones, dialkyl-1,3-diketones, alkyl-β-keto esters, terminal alkines, linear or cyclic 1,3-thioethers, dialkyl phosphonates, dialkyl malonic acid esters, β-cyano carbonic acids and their respective alkylesteres, β-alkoxy carbonic acids and their respective alkylesters, β-cyano nitriles, cyclopentadiene, substituted cyclopentadiene, trialkylimines, dialkylimines, diaryl ketones, alkyl-aryl-ketones, diaryl-1,3-diketones, alkyl-aryl-1,3-diketones, β-aryloxy carbonic acids and their respective alkylesters, β-aryloxy carbonic acids and their respective arylesters, aryl-β-ketoesters, diarylphosphonates, alkyl-aryl-phosphonates, diaryl malonic acid esters, alkyl-aryl-malonic acid esters, β-cyano carbonic acids arylesteres and arylimines.

According to an exemplary embodiment of the method of synthesizing organic molecules the ionic liquid satisfy the generic formula $[Q^+]_a[A^{a-}]$, wherein $[A^{a-}]$ is a carbanion formed by deprotonating a chemical compound out of the group consisting of: acetoacetic ester, malonic mononitrile, malonic acid dimethylester, malonic acid diethylester, acetylacetone, malonic acid dinitrile, acetone, diethylketone, methlethylketone, dibutylketone, 1,3-dithian, acetaldehyde, benzaldehyde, crotonaldehyde and butyraldehyde.

According to an exemplary embodiment of the method of synthesizing organic molecules the ionic liquid satisfy the generic formula $[Q^+]_a[A^{a-}]$, wherein $[Q^+]$ is selected out of the group consisting of: 1,3-dialkylimidazolium, 1,3-dialkylbenzimidazolium, 1-benzyl-3-alkylimidazolium, 1-benzyl-2,3-dialkylimidazolium, 1,2,3-trialkylimidazolium, N-alkyloxazolium, N-alkylthiaozolium, methyltrialkylammonium, tetraalkylphosphonium, trialkylsulfonium, N-alkylpyridinium, N-alkyl-4-alkyl-pyridinium, N,N-dialkylpiperidinium, N,N-dialkylmorpholinium and N,N-dialkylpyrrolidinium, 1,3-dmethylimidazolium, 1,2,3-trimethylimidazolium, 1-ethyl-3-methylimidazolium, 1-ethyl-2,3-dimethyl-imidazolium, 1-propyl-3-methylimidazolium, 1-butyl-3-methylimidazolium, 1-octyl-3-methylimidazolium, triethylmethylammonium, tributylmethylammonium, trioctylmethylammonium, triethylmethylphosphonium, tributylmethylphosphonium, and trioctylmethylphosphonium.

According to an exemplary embodiment the method of synthesizing organic molecules further comprises adding an additive before synthesizing the organic molecules.

According to an exemplary embodiment of the method of synthesizing organic molecules the additive is selected out of the group consisting of: catalysts, emulsifying agents, demulsifying agents, corrosion protection agents, defoaming agents, antioxidants, pH-value stabilizing agents, acid capture agents, and an additional ionic liquid.

In particular, the additional ionic liquid may have a lower or higher viscosity so that by adding the additional ionic liquid the viscosity may be adjusted or set to a desired value.

According to an exemplary embodiment the method of synthesizing further comprises separating the organic molecules and the mixture of the electrophilic educt and the ionic liquid.

In particular, the separating may be performed by distillation, vacuum distillation, which may be suitable methods since the ionic liquid has a very low or no measurable vapor pressure. According to other embodiments the separation may be performed by phase separation, which may either be suitable in case the organic molecules or organic product may have a miscibility gap, or when using an additive, e.g. in cases the ionic liquid mixes with water while the organic product does not mixes with water. Another process for the separation may be extraction of the organic molecules.

The aspects defined above and further aspects of the invention are apparent from the examples of embodiment to be described hereinafter and are explained with reference to these examples of embodiment. It should be noted that features described in connection with one exemplary embodiment or exemplary aspect may be combined with other exemplary embodiments and other exemplary aspects.

DESCRIPTION OF EMBODIMENTS

In the following some details concerning the production or forming of ionic liquids by performing a deprotonation step. The above described carbanions may be produced by deprotonating a C—H acid using a primary ionic liquid. In particular, according to an exemplary aspect a method of producing an ionic liquid comprising a carbanion including a first ion is provided, wherein the method comprises providing a primary ionic liquid comprising the first ion as a cation and a base as an anion, and mixing the primary ionic liquid with a C—H acid. For example, the base may be strong enough and may be denoted by $[B^-]$ while the first ion may be denoted $[Q^+]$. Preferred anions may be hydroxide, alkoxide, hydrogencarbonate, carbonate, alkylcarbonate, arylcarbonate, carboxylate like acetate. The primary ionic liquid may react with a respective C—H acid by forming the carbanion and the protonated anion BH. The respective reactions may be described by:

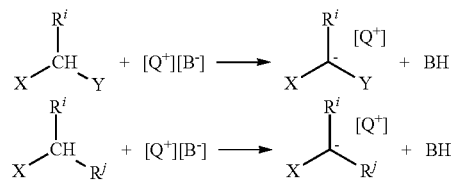

The respective reaction may be performed under known conditions. In particular, the reaction may be performed batch-wise, semi-continuous or continuous. The mixture may be rocked, shaked, stirred, or mixed in any other way. Furthermore, the mixture may be cooled or heated in order to adjust the temperature for the reaction. The reaction mixture may be conditioned by using common processes like distillation, vacuum distillation, thin film evaporation, rotation evaporation, spray drying, osmosis, pervaporation, stripping by using gas or water vapor, freeze desalination, freeze-drying, chemical or physical adsorption, or other processes. Volatile components may be removed at a temperature less than 100° C., particularly at temperatures less than 70° C. and preferably at temperatures less than 50° C. If necessary, reduced pressure may be used. Additionally, remaining educts and/or remaining catalysts or any other remaining agents or components may be removed by extraction. Possible solvents for this removing may be one of the following solvents: pentane, hexane, heptane, octane, nonane, decane, petroleum ether, benzine, diesel, benzol, toluol, o-xylol, m-xylol, p-xylol, ether as diethylether, tetrahydrofurane, ester as ethylacetate, methylacetate, chlorinated hydrocarbons as chloroform or dichloromethane, or mixtures thereof. Additionally additives may be used, e.g. an alcohol like methanol, ethanol, isopropanol, n-propanol, n-butanol, sec-butanol, tert-butanol, pentanol, hexanol, heptanol or octanol, an ether like diethylether or tetrahydrofurane, a dialkylformamide like dimethylformamide or diethylformamide, a keton like acetone or methylethylketon, a sulfoxide like dimethylsulfoxide, or a nitrile like acetonnitrile or a mixture thereof.

For example, 1-butyl-3-methylimidazolium-acetyl-acetonate may be produced according to the following reaction:

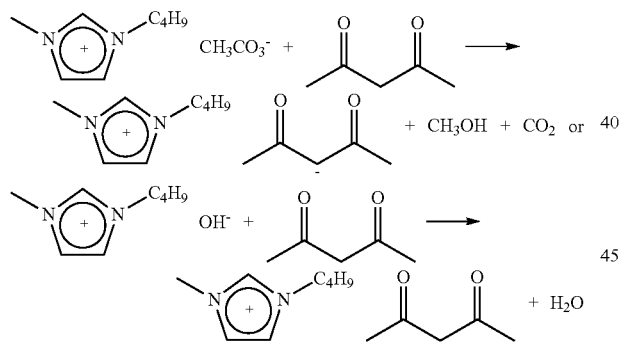

In the first case a methanolic solution of the quite stable 1-butyl-3-methylimidazolium-methylcarbonate is stirred for several hours at room temperature while an excess of acetylacetone is present in the solution. A release of carbon dioxide may clearly indicate the reaction. The excess of acethylacetone and the methanol may be removed (in vacuo) in a rotation evaporator so that 1-butyl-3-methylimidazolium-acetylacetonate is obtained as a viscosuos liquid having a light yellow color and a refractive index of $n_D^{20}=1,4645$.

The liquid may be stocked for a long time, e.g. months. Alternatively it may be possible to use 1-butyl-3-methylimidazolium-hydroxide.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The mere fact that certain measures are recited in mutually different dependent claims does not indicate that a combination of these measures cannot be used to advantage.

The invention claimed is:
1. A method of synthesizing organic molecules, the method comprising:
   providing an electrophilic educt,
   providing an ionic liquid wherein an anion of the ionic liquid is a carbanion, and wherein the carbanion of the ionic liquid is an educt, and
   mixing the electrophilic educt and the ionic liquid, whereby the electrophilic educt reacts with the carbanion, thereby synthesizing the organic molecules.
2. The method according to claim 1,
   wherein the carbanion can be described by one of the following structures:

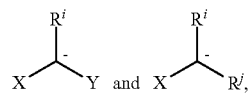

wherein X and Y indicate functional groups selected from groups that attract electrons due to the inductive effect, groups that attract electrons due to the mesomeric effect, groups that delocalize electrons, and groups that localize electrons, wherein $R^i$ is H when X and Y are present and $R^i$ is H or alkyl when $R^j$ is present, and wherein $R^j$ is H.
3. The method according to claim 1,
   wherein the ionic liquid satisfies the generic formula $[Q^+]_a[A^{a-}]$,
   wherein $[A^{a-}]$ is a carbanion formed by deprotonating a chemical compound selected from the group consisting of:
   dialkyl ketones, dialkyl 1,3-diketones, diaryl 1,3-diketones, alkyl-β-keto esters, terminal alkenes, linear or cyclic 1,3-thioethers, dialkyl phosphonates, dialkyl malonic acid esters, β-cyano carboxylic acids and their respective alkyl esters and aryl esters, β-alkoxy carboxylic acids and their respective alkyl β-cyano nitriles, cyclopentadiene, substituted cyclopentadiene, trialkylimines, dialkylimines, alkyl-aryl-ketones, diaryl-1,3-diketones, alkyl-aryl-1,3-diketones, β-aryloxy carboxylic acids and their respective alkyl esters and aryl esters, aryl-β-ketoesters, diarylphosphonates, alkyl-aryl-phosphonates, diaryl malonic acid esters, and alkyl-aryl-malonic acid esters.
4. The method according to claim 1,
   wherein the ionic liquid satisfies the generic formula $[Q^+]_a[A^{a-}]$,
   wherein $[A^{a-}]$ is a carbanion formed by deprotonating a chemical compound selected from the group consisting of:
   acetoacetic ester, malonic mononitrile, malonic acid dimethylester, malonic acid diethylester, acetylacetone, malonic acid dinitrile, acetone, diethylketone, methlethylketone, dibutylketone, 1,3-dithiane, acetaldehyde, crotonaldehyde, and butyraldehyde.
5. The method according to claim 1, wherein the ionic liquid satisfies the generic formula $[Q^+]_a[A^{a-}]$, wherein $[Q^+]$ is selected from the group consisting of: 1,3-dialkylimidazolium, 1,3-dialkylbenzimidazolium, 1-benzyl-3-alkylimidazolium, 1-benzyl-2,3-dialkylimidazolium, 1,2,3-trialkylimidazolium, N-alkyloxazolium, N-alkylthiazolium, methyltrialkylammonium, tetraalkylphosphonium, trialkylsulfonium, N-alkylpyridinium, N-alkyl-4-alkyl-pyridinium, N,N-dialkylpiperidinium, N,N-dialkylmorpholinium, N,N-dialkylpyrrolidinium, 1,3-dimethylimidazolium, 1,2,3-trimethylimidazolium, 1-ethyl-3-methylimidazolium, 1-ethyl-2,3-dimethylimidazolium, 1-propyl-3-methylimidazolium, 1-butyl-3-methylimidazolium, 1-octyl-3-methylimidazolium, triethylmethylammonium, tributylmethylammonium, trioctylmethylammonium, triethylmethylphosphonium, tributylmethylphosphonium, and trioctylmethylphosphonium.

6. The method according to claim 1, further comprising:

adding an additive before synthesizing the organic molecules.

7. The method according to claim 6, wherein the additive is selected from the group consisting of: catalysts, emulsifying agents, demulsifying agents, corrosion protection agents, defoaming agents, antioxidants, pH-value stabilizing agents, acid capture agents, and an additional ionic liquid.

8. Method according to claim 1, further comprising:

separating the organic molecules and the mixture of the electrophilic educt and the ionic liquid.

* * * * *